United States Patent
Woods (10) Patent No.: US 11,871,967 B1
(45) Date of Patent: Jan. 16, 2024

(54) PEDICLE SCREW DEVICE AND METHOD OF USE

(71) Applicant: Vertrae Medical Consulting, LLC, Dayton, OH (US)

(72) Inventor: Kamal R. Woods, Dayton, OH (US)

(73) Assignee: Vertrae Medical Consulting, LLC, Dayton, OH (US)

( * ) Notice: Subject to any disclaimer, the term of this patent is extended or adjusted under 35 U.S.C. 154(b) by 0 days.

(21) Appl. No.: 18/115,277

(22) Filed: Feb. 28, 2023

(51) Int. Cl.
*A61B 17/70* (2006.01)
*A61B 17/00* (2006.01)

(52) U.S. Cl.
CPC .. *A61B 17/7032* (2013.01); *A61B 2017/0092* (2013.01)

(58) Field of Classification Search
CPC .................................................. A61B 17/7032
See application file for complete search history.

(56) References Cited

U.S. PATENT DOCUMENTS

| | | |
|---|---|---|
| 9,918,746 B2 | 3/2018 | Beyar et al. |
| 10,278,737 B2 | 5/2019 | Smith |
| 10,682,204 B2 | 6/2020 | Kieser et al. |
| 2009/0149862 A1 | 6/2009 | Kim |
| 2009/0210000 A1 | 8/2009 | Sullivan et al. |
| 2018/0317971 A1* | 11/2018 | Prevost .............. A61B 17/8635 |
| 2019/0167310 A1 | 6/2019 | Felix et al. |

FOREIGN PATENT DOCUMENTS

| WO | 2017186799 A1 | 11/2017 |
|---|---|---|
| WO | 2022002908 A1 | 1/2022 |

* cited by examiner

*Primary Examiner* — Andrew Yang
(74) *Attorney, Agent, or Firm* — Stevens & Showalter LLP (57) ABSTRACT

A pedicle screw for insertion into a vertebra, the pedicle screw including: a head; a distal tip; a threaded portion extending at least partially between the head and the distal tip; and a radiographically visible element located at a predefined location on the threaded portion, where the head, the distal tip, and the threaded portion are formed of a metal or a metal alloy. Also disclosed is a corresponding system for insertion of a pedicle screw into a vertebra and a corresponding method for inserting a pedicle screw into a vertebra.

10 Claims, 10 Drawing Sheets

PEDICLE SCREW DEVICE AND METHOD OF USE

BACKGROUND

The present disclosure relates generally to a pedicle screw, systems, and methods for inserting a pedicle screw into a vertebra, specifically to determining the optimal insertion angle for the pedicle screw using a radiographically visible element.

Pedicle screws may be used to secure vertebrae in spinal fusion procedures. These surgeries have become minimally invasive procedures that use fluoroscopy and x-ray imaging to assist with placement of the pedicle screw at the desired location within the vertebra. Correct placement of the pedicle screw is crucial to avoid serious complications. However, even with such imaging, it can still be difficult to accurately predict whether the pedicle screw will be correctly placed. Conventional devices and methods that help determine the correct placement of the pedicle screw often involve computers and complex, robotic machinery, which are high in cost and may not be available in all settings. Additionally, these conventional methods may include the use of a guide wire or guide pin, which is inserted into the vertebra prior to the insertion of the pedicle screw. However, the use of a guide wire or guide pin may increase the duration and complexity of the procedure.

BRIEF SUMMARY

In accordance with one aspect of the present disclosure, a pedicle screw for insertion into a vertebra comprises a head; a distal tip; a threaded portion extending at least partially between the head and the distal tip; and a radiographically visible element located at a predefined location on the threaded portion, wherein the head, the distal tip, and the threaded portion are formed of a metal or a metal alloy.

In accordance with another aspect of the present disclosure, a system for insertion of a pedicle screw into a vertebra comprises a pedicle screw, wherein the pedicle screw comprises a head; a distal tip; a threaded portion extending at least partially between the head and the distal tip; and a radiographically visible element located at a predefined location on the threaded portion; an insertion tool configured to insert the pedicle screw into the vertebra; and a radiographic imaging device configured to image the radiographically visible element with respect to the distal tip, wherein the predefined location is a first distance from the distal tip, and wherein the pedicle screw is configured such that an optimal angle for insertion of the pedicle screw into the vertebra is indicated when the first distance corresponds with a second distance between two vertebral landmarks.

In accordance with another aspect of the present disclosure, a method for inserting a pedicle screw into a vertebra comprises introducing a pedicle screw into a soft tissue of a patient, wherein the pedicle screw comprises a head; a distal tip; a threaded portion extending at least partially between the head and the distal tip; and a radiographically visible element located at a predefined location on the threaded portion; capturing a first radiographic image of the pedicle screw with respect to the vertebra; determining a first distance in the first radiographic image, wherein the first distance is between the distal tip and the radiographically visible element; determining a second distance in the first radiographic image, wherein the second distance is between a first anatomical landmark of a pedicle of the vertebra and a second anatomical landmark of a pedicle of the vertebra; comparing the first distance and the second distance; and when the first distance is equal to the second distance, determining that a current insertion angle is optimal, and at least partially inserting the pedicle screw into the vertebra along the current insertion angle.

DETAILED DESCRIPTION

The above-discussed issues with current pedicle screw insertion systems and methods are addressed by the pedicle screw, system, and methods of the present disclosure. As described herein, the pedicle screw may comprise a radiographically visible element, which assists with correct placement of the pedicle screw. The radiographically visible element may be located at a predefined distance from a distal tip of the pedicle screw, where the predefined distance corresponds with a distance between anatomical landmarks of the vertebra. The pedicle screw, system, and method described herein utilizes these distances and may be performed by a surgeon to ensure more accurate placement of the pedicle screw without the use of a guide wire/pin, computers, or robots, minimizing the cost, complexity, and length of the procedure and avoiding the use of expensive and/or inaccessible equipment.

"Radiographically Visible Element" as used herein is an element that, while inside a human body, can be viewed with a radiographic imaging device, such as a fluoroscopy or x-ray device.

As used herein, an element is "Visually Distinct" if the element can be distinguished from its surroundings when visualized in a radiographic image.

Figure 1:
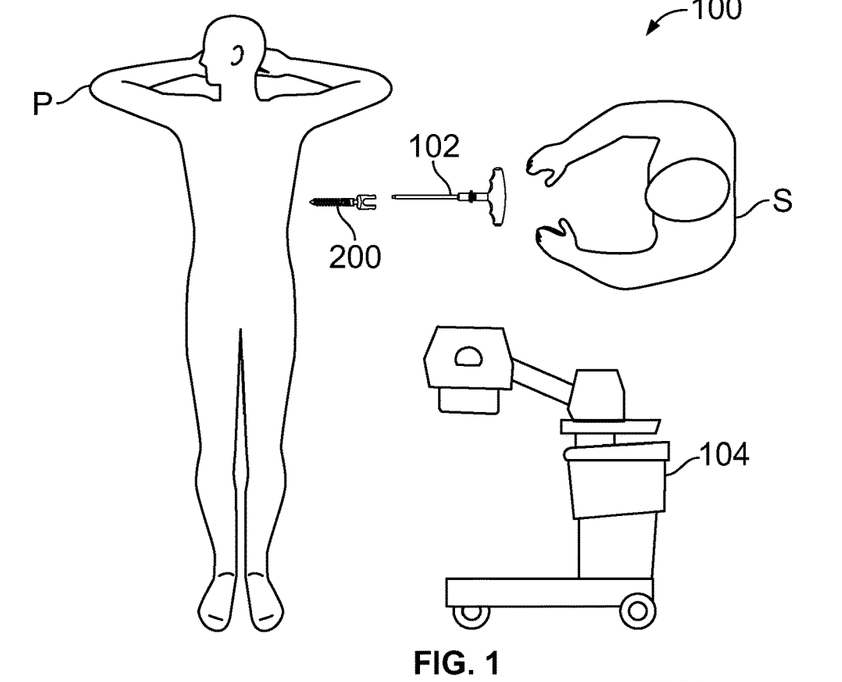
FIG. 1 is a schematic diagram of a system, in accordance with the present disclosure.

With reference to the drawings, FIG. 1 depicts a system 100 in accordance with the present disclosure. The system 100 may be used by a surgeon S to operate on a patient P, specifically to insert one or more pedicle screws into one or more vertebra of the patient P. The system may comprise a pedicle screw 200 as described herein, an insertion tool 102 configured to insert the pedicle screw 200 into the vertebra, and a radiographic imaging device 104 configured to image the pedicle screw 200. While not shown, the system 100 may be used with conventional surgical items such as, for example, an operating table, an anesthesia machine, a suction machine, scalpels, sutures, etc. As discussed below with reference to FIGS. 2A and 2B, the pedicle screw 200 may comprise a radiographically visible element that may be used by the surgeon S to determine an optimal angle for inserting the pedicle screw 200 into a vertebra of the patient P. Once the optimal angle is found, the pedicle screw 200 may be inserted into the vertebra of the patient P using the insertion tool 102. As shown in FIG. 1, the insertion tool 102 may be a manual or powered screwdriver device. Additionally, the insertion tool 102 may be an electric screwdriver. As discussed in detail below, the surgeon S may use the radiographic imaging device 104 to view the radiographically visible element of the pedicle screw 200 and use the radiographically visible element to determine the optimal insertion angle. The radiographic imaging device 104 may be a fluoroscopy device or an x-ray device.

FIGS. 2A-2E illustrate examples of a pedicle screw 200A-200E for insertion into a vertebra, in accordance with the present disclosure. The pedicle screw 200A-200E may have a head 202 and a distal tip 204. The head 202 and the distal tip 204 may be separated by a threaded portion 206, which extends at least partially between the head 202 and the distal tip 204 along a longitudinal axis L of the pedicle screw 200A-200E. The head 202, the distal tip 204, and the threaded portion 206 may be formed of one or more metals and/or metal alloys. For example, the head 202, the distal tip 204, and the threaded portion 206 may be formed of titanium. In some particular examples, the pedicle screw 200A-200E may consist entirely of one or more metals and/or metal alloys such as titanium.

Figure 2A:
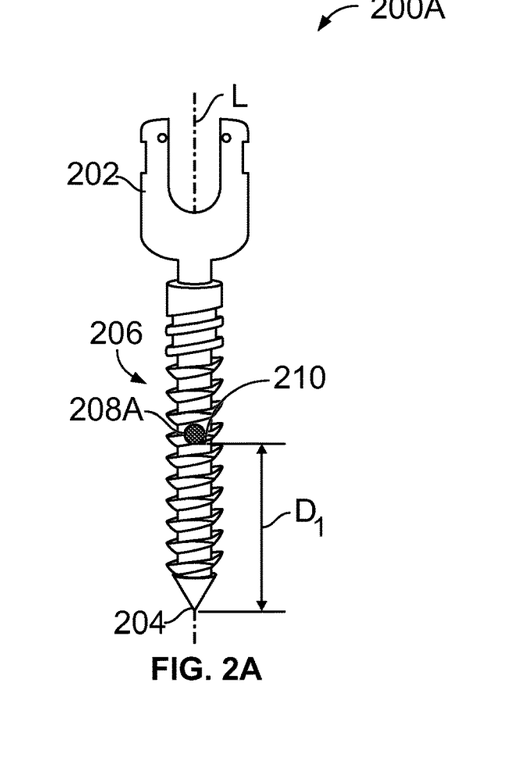
FIGS. 2A-2E are illustrations of a pedicle screw, in accordance with the present disclosure.

With reference to FIG. 2A, the pedicle screw 200A may comprise at least one radiographically visible element 208A that is disposed on the threaded portion 206 at a predefined location 210. The radiographically visible element 208A may be a radiographically visible marker that is visually distinct from the threaded portion 206. In some examples, the radiographically visible marker may be added to the threaded portion 206, such as a radiopaque paint or coating applied to a surface of the threaded portion 206. In other examples, the radiographically visible marker may be incorporated into the threaded portion 206, such as a visually distinct material (e.g., a different metal, metal alloy, or other material) that is incorporated into the threaded portion 206 during manufacture of the pedicle screw 200A. Although a substantially circular radiographically visible element 208A is depicted in FIG. 2A, the radiographically visible element 208A may comprise any suitable shape, such as an oval, diamond, etc. The radiographically visible element 208A may at least partially encircle the threaded portion 206 and/or may comprise multiple discrete elements at least partially encircling the threaded portion 206 so that the radiographically visible element 208A is visible from different views and/or angles.

Figure 2B:
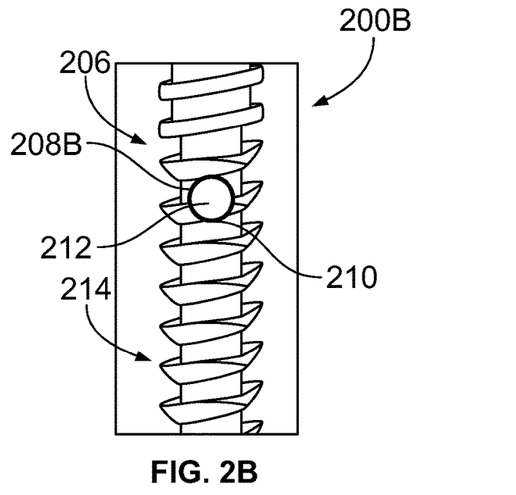
Figure 2C:
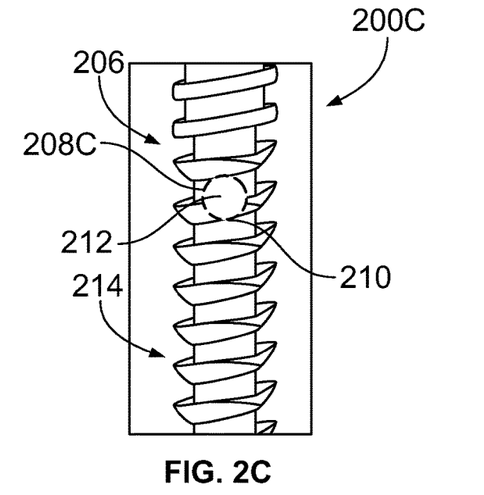

FIGS. 2B-2E illustrate radiographically visible elements 208B-208E that are defined by a hollow portion 212 of the respective pedicle screw 200B-200E, in which the hollow portion 212 is visually distinct from a solid portion 214 of the pedicle screw 200B-200E and the predefined location 210 is located where the hollow portion 212 abuts the solid portion 214. As shown in FIG. 2B, the radiographically visible element 208B may comprise a substantially circular hollow portion 212 of the pedicle screw 200B. The hollow portion 212 in FIG. 2B may extend either partially or entirely through the threaded portion 206 in a direction perpendicular to the longitudinal axis (not labeled in FIG. 2B; see FIG. 2A). In the example shown in FIG. 2C, radiographically visible element 208C may comprise a hollow portion 212 with a spherical shape formed in an interior of the pedicle screw 200C.

Figure 2D:
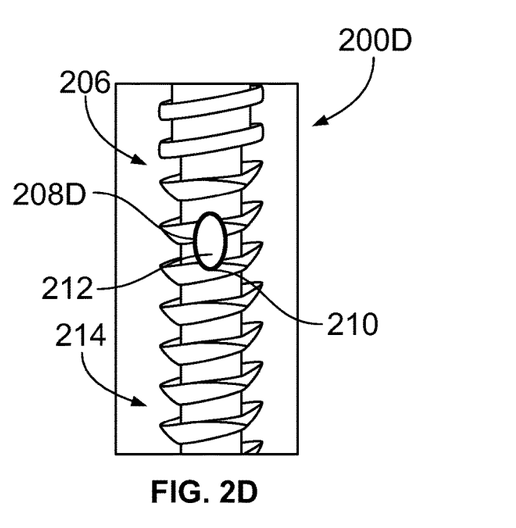

As shown in FIG. 2D, the radiographically visible element 208D may comprise a hollow portion 212 with an oval shape. The hollow portion 212 may extend either partially or entirely through the threaded portion 206. Alternatively, in another example (not shown), the hollow portion 212 may comprise an ovoid shape that is formed in an interior of the pedicle screw 200D. In either example, the hollow portion 212 may be formed in the pedicle screw 200D such that a major axis (not labeled) of the oval or ovoid shape is parallel with the longitudinal axis (not labeled in FIG. 2D; see FIG. 2A) as shown in FIG. 2D or perpendicular to the longitudinal axis.

Figure 2E:
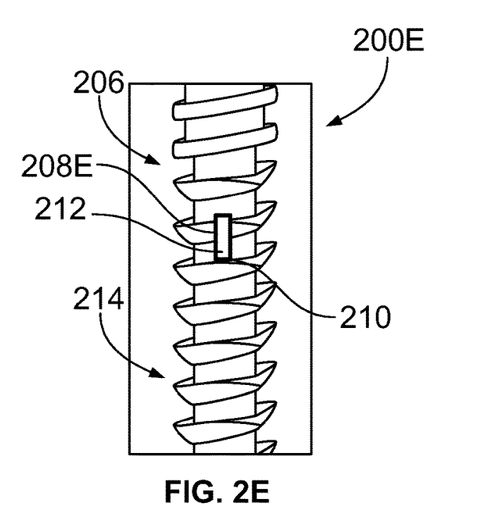

As shown in FIG. 2E, the radiographically visible element 208E may comprise a hollow portion 212 with a linear shape. The hollow portion 212 may extend either partially or entirely through the threaded portion 206 in a direction that is parallel to the longitudinal axis (not labeled in FIG. 2E; see FIG. 2A). In some examples (not shown), the linear shape may be formed in an interior of the pedicle screw 200E, e.g., as a substantially cylindrical hollow portion extending along the longitudinal axis. Other types of visually distinct, radiographically visible elements may also be used, alone or in conjunction with the radiographically visible elements 208A-208E described herein.

In the pedicle screws 200A-200E shown in FIGS. 2A-2E, the predefined location 210 may be located a first distance D1 from the distal tip 204. In some examples, the first distance D1 may be 20 mm. As discussed in detail below, the pedicle screw 200A-200E may be configured such that an optimal angle for insertion of the pedicle screw 200A-200E is indicated when the first distance D1 corresponds with a second distance between two vertebral landmarks. In particular, the pedicle screw 200A-200E may be configured such that a radiographic imaging device (not shown in FIGS. 2A-2E; see 104 in FIG. 1) can image the radiographically visible element 208A-208E with respect to the distal tip 204, with the first distance D1 between the distal tip 204 and the radiographically visible element 208A-208E providing a reference point for determining whether the pedicle screw 200A-200E is at the optimal angle and location to provide correct placement within the vertebra.

Figure 3A:
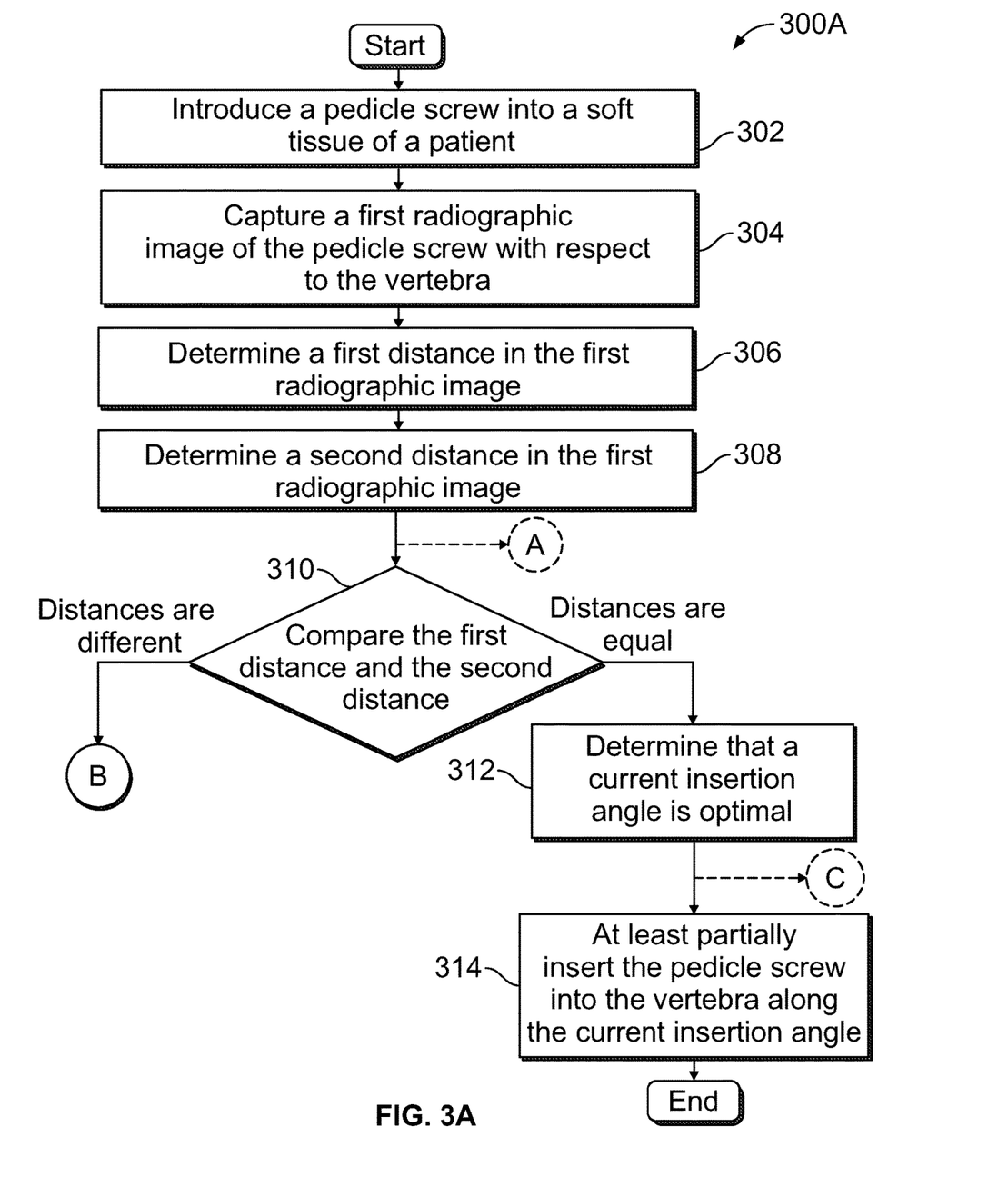
FIGS. 3A-3E are flowcharts illustrating processes for inserting a pedicle screw into a vertebra, in accordance with the present disclosure.

FIGS. 3A-3E illustrate exemplary methods 300A-300E for inserting a pedicle screw into a vertebra, in accordance with the present disclosure. The methods 300A-300E may be used in conjunction with the pedicle screws 200A-200E depicted in FIGS. 2A-2E and described herein. With reference to the method 300A in FIG. 3A, a pedicle screw in accordance with the present disclosure is introduced into the soft tissue of a patient at 302. In some examples, the pedicle screw is introduced until the distal tip touches, but does not enter, the vertebra. At 304, a first radiographic image of the pedicle screw is captured in a first view with respect to the vertebra, and at 306, a first distance D1 is determined in the first radiographic image. As discussed above with respect to FIGS. 2A, and 2B, the first distance D1 is between the distal tip 204 and the radiographically visible element 208 of the pedicle screw 200A-200E. As shown in FIG. 3A, a second distance D2 is determined in the first radiographic image at 308. As discussed below with respect to FIGS. 4A and 4B, the second distance D2 is between a first and a second anatomical landmark of a pedicle of the vertebra. With reference to FIG. 3A, at 310, the first distance and the second distance are compared to each other. When the first distance and the second distance are equal, it is determined at 312 that a current insertion angle is optimal. At 314, the pedicle screw is then at least partially inserted into the vertebra along the current insertion angle, after which the method 300A may conclude.

Figure 3B:
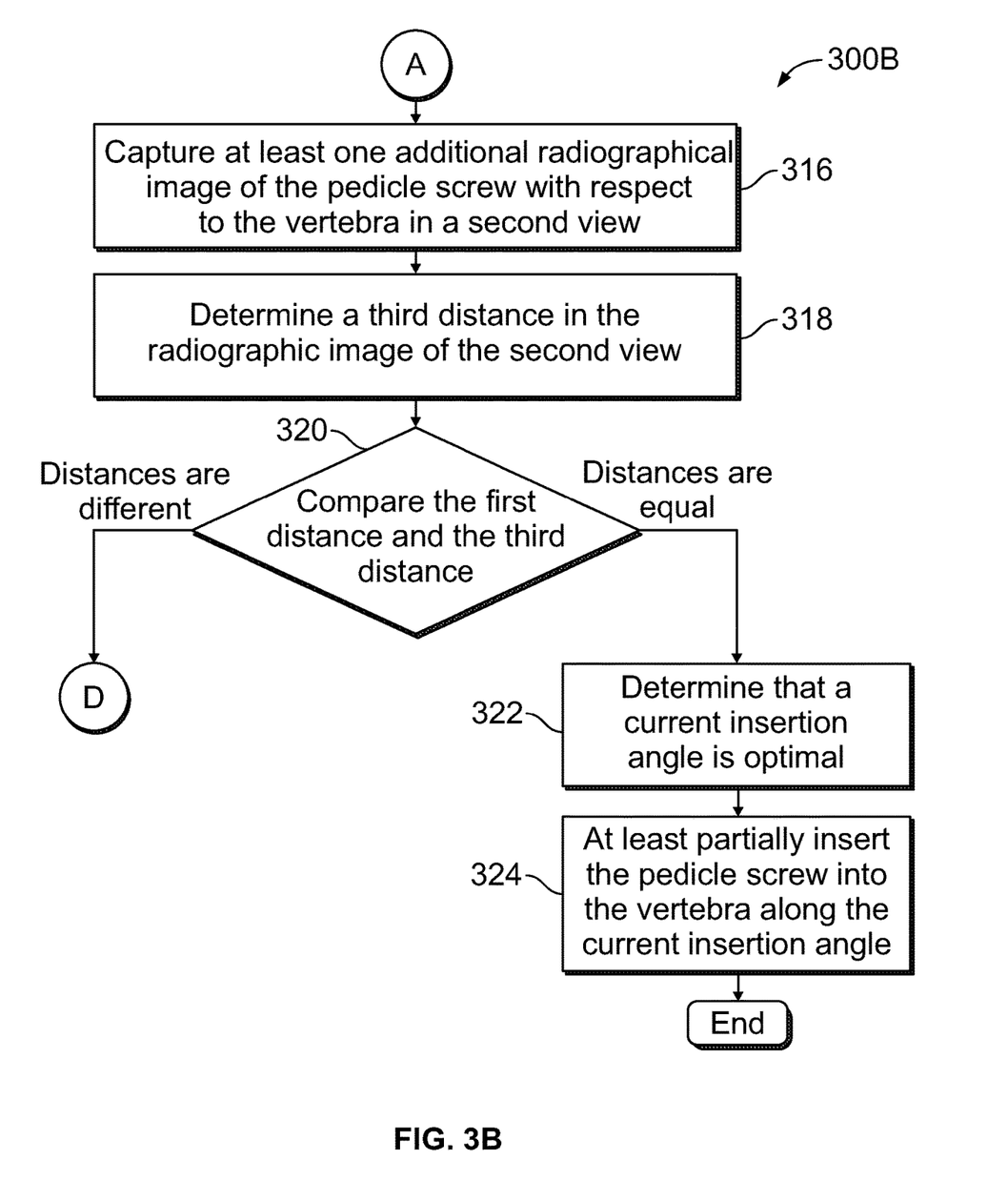

As shown in FIG. 3A, the method 300A may optionally proceed to A. While A is shown as occurring after the second distance is determined at 308, the method 300A may proceed to A at any point after the first radiographic image is captured at 304, but prior to the at least partial insertion of the pedicle screw at 314. FIG. 3B illustrates the method 300B, which starts at A in FIG. 3A. At 316, at least one additional radiographical image of the pedicle screw is captured in a second view with respect to the vertebra, in which the second view is different from the first view. As discussed below with respect to FIGS. 4A-5B, the first and second views may comprise, for example, an anteroposterior (AP) view and a lateral view. As shown in FIG. 3B, a third distance is determined in the radiographic image of the second view at 318. As discussed below with reference to FIGS. 5A and 5B, the third distance D3 may be between a third and fourth anatomical landmark of the pedicle of the vertebra. With reference to FIG. 3B, at 320, the first distance and the third distance are compared to each other. If the first distance and the third distance are equal, it is determined at 322 that a current insertion angle is optimal. At 324, the pedicle screw is then at least partially inserted into the vertebra along the current insertion angle, after which the method 300B may conclude.

Figure 3C:
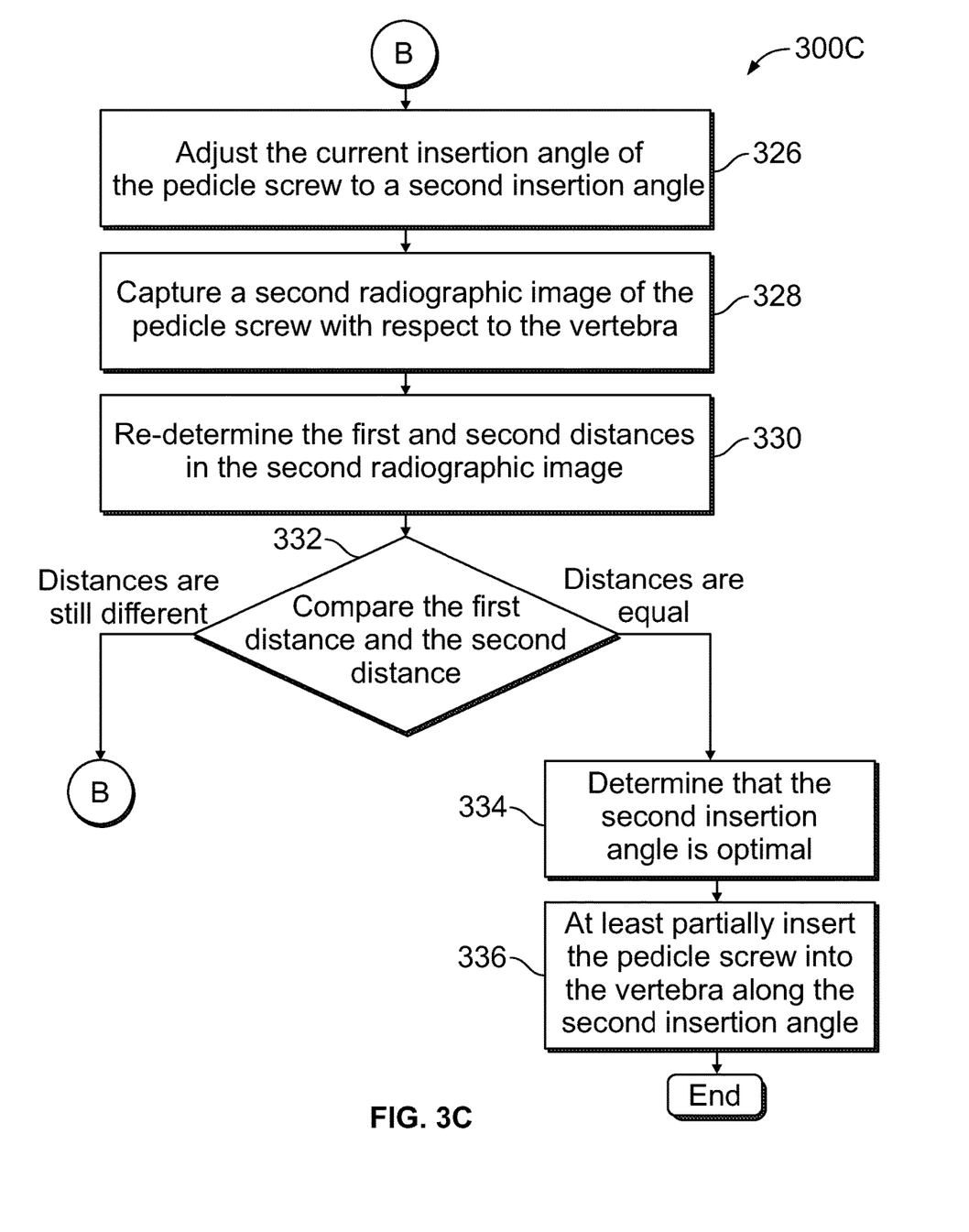

As shown in FIG. 3A, when the first distance and the second distance are different, the method 300A may proceed to B. FIG. 3C illustrates method 300C, which starts at B in FIG. 3A. At 326, the current insertion angle of the pedicle screw is adjusted to a second insertion angle. After adjusting the pedicle screw to the second insertion angle, a second radiographic image of the pedicle screw with respect to the vertebra is captured at 328. The second radiographic image may be the same view as the first radiographic image or a different view. At 330, the first distance and the second distance are re-determined in the second radiographic image, and the first distance and the second distance are compared to each other at 332. When the first distance and the second distance obtained from the second radiographic image are equal, it is determined at 334 that a current insertion angle is optimal. At 336, the pedicle screw is then at least partially inserted into the vertebra along the second insertion angle, after which the method 300C may conclude. Alternatively, when the first distance and the second distance as measured in the second radiographic image are still different, the method 300C may return to B and repeat the method 300C. The method 300C may be repeated as many times as needed to achieve the optimal insertion angle.

Figure 3D:
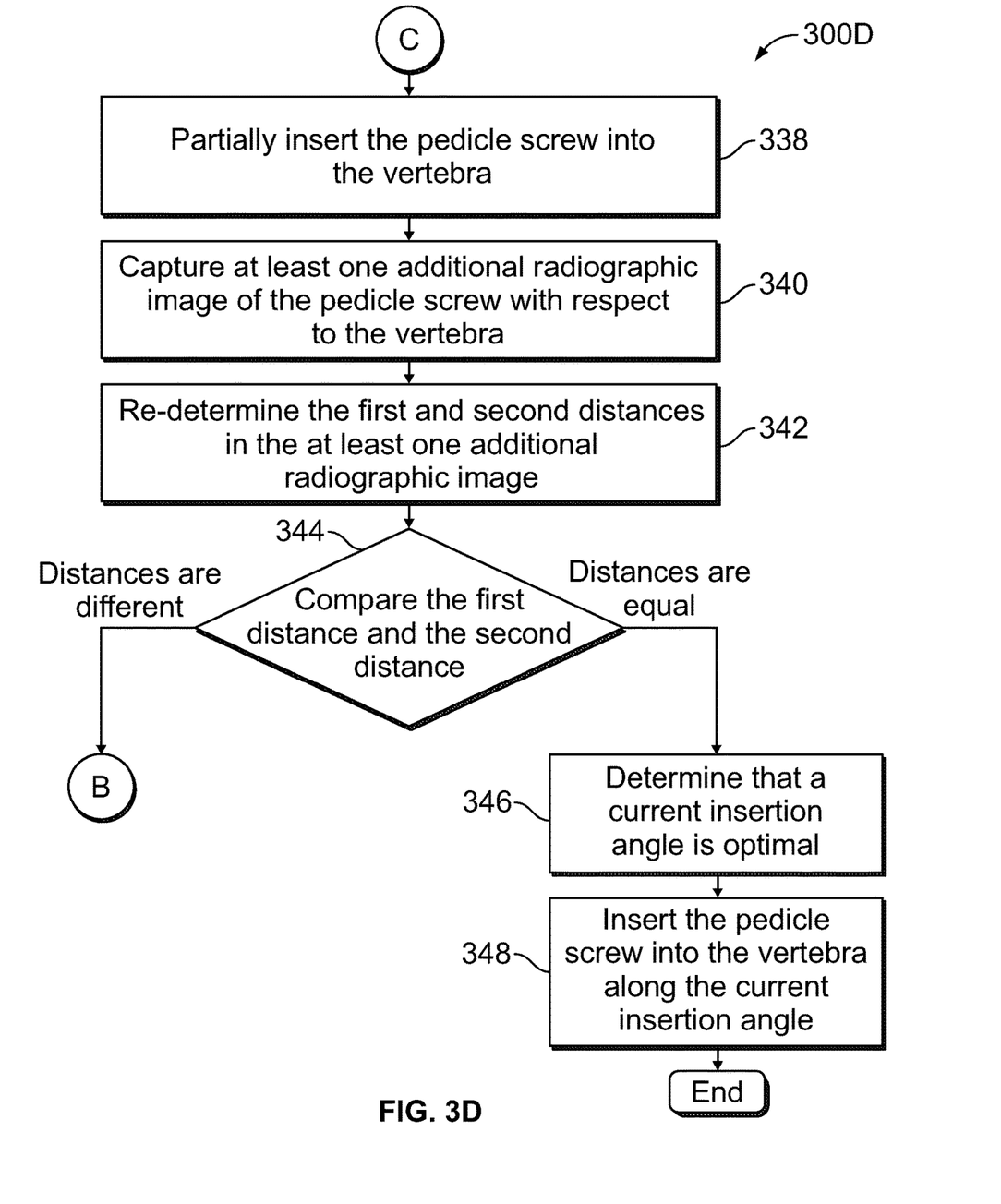

As shown in FIG. 3A, the method 300A may optionally proceed to C after it is determined that the current insertion angle is optimal at 312. FIG. 3D illustrates method 300D, which starts at C in FIG. 3A. At 338, the pedicle screw is partially inserted into the vertebra. At 340, after partially inserting the pedicle screw, at least one additional radiographic image of the pedicle screw with respect to the vertebra is captured. At 342, the first distance and the second distance in the at least one additional radiographic image are re-determined, and the first distance and the second distance are compared at 344. When the first distance and the second distance are equal, it is determined at 346 that the current insertion angle is optimal. At 348, the pedicle screw is inserted into the vertebra along the current insertion angle, after which the method 300D may conclude. Alternatively, when the first distance and the second distance are different, the method 300D may proceed to B, as described above with respect to FIG. 3C. In some examples, adjusting the current insertion angle of the pedicle screw after partial insertion may be performed while the pedicle screw remains at least partially inserted into the vertebra. In other examples, adjusting the current insertion angle of the pedicle screw may include removing the pedicle screw fully or partially from the vertebra.

Figure 3E:
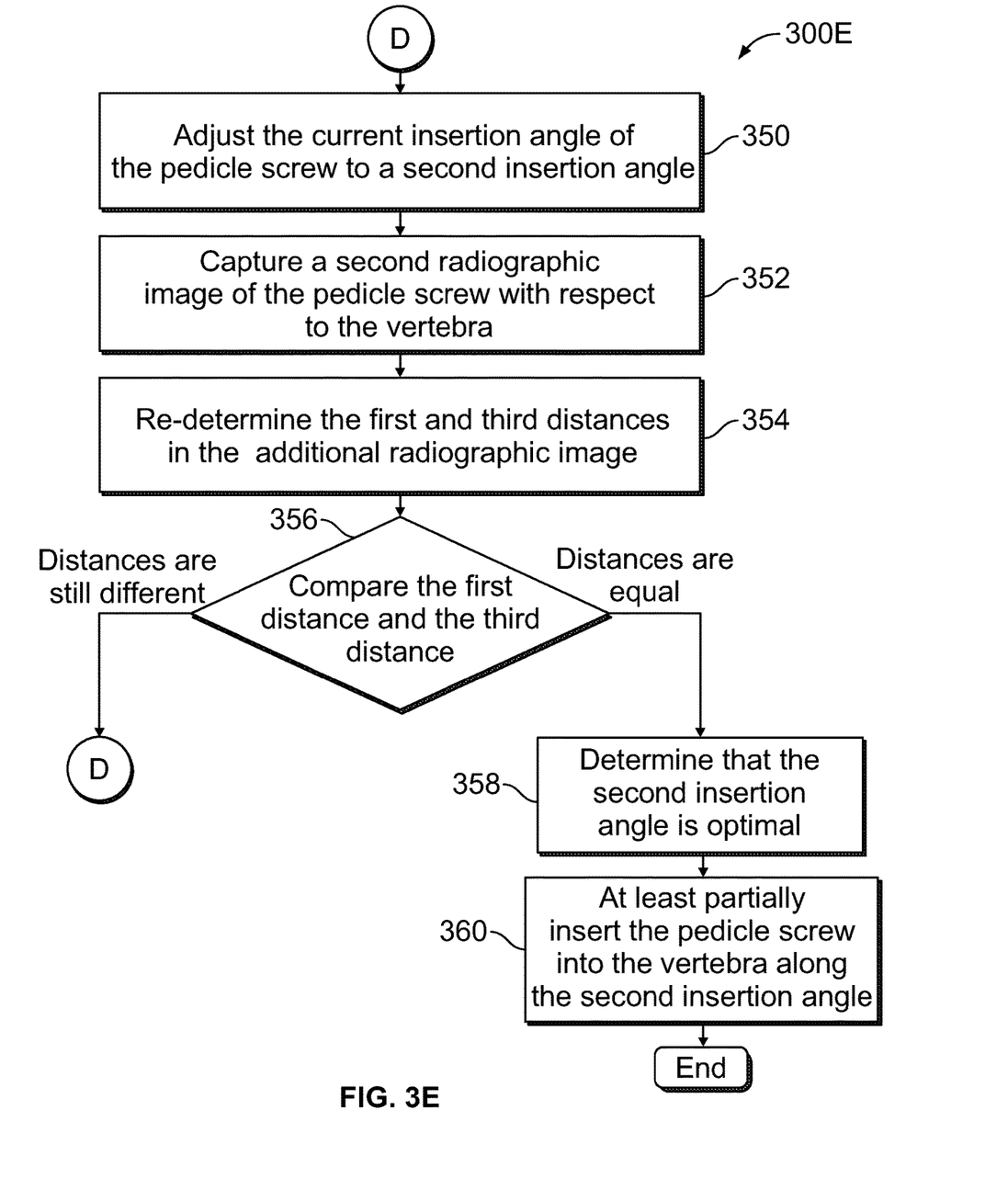

As shown in FIG. 3B, when the first distance and the third distance are different in the additional radiographic image, the method 300B may proceed to D. FIG. 3E illustrates the method 300E, which begins at D in FIG. 3B. At 350, the current insertion angle of the pedicle screw is adjusted to a second insertion angle, and a further radiographic image of the pedicle screw with respect to the vertebra is captured at 352. The further radiographic image may comprise an image in the first view or the second view. At 354, the first distance and the third distance are re-determined in the further radiographic image, and at 356, the first distance and the third distance are compared to each other. When the first distance and the third distance are equal, it is determined that the second insertion angle is optimal at 358. At 360, the pedicle screw is at least partially inserted into the vertebra along the second insertion angle, after which the method 300E may conclude. Alternatively, if the first distance and the third distance are still different, the method 300E returns to D and repeats the method 300E. The method 300E may be repeated as many times as needed to achieve the optimal insertion angle.

Figure 4:
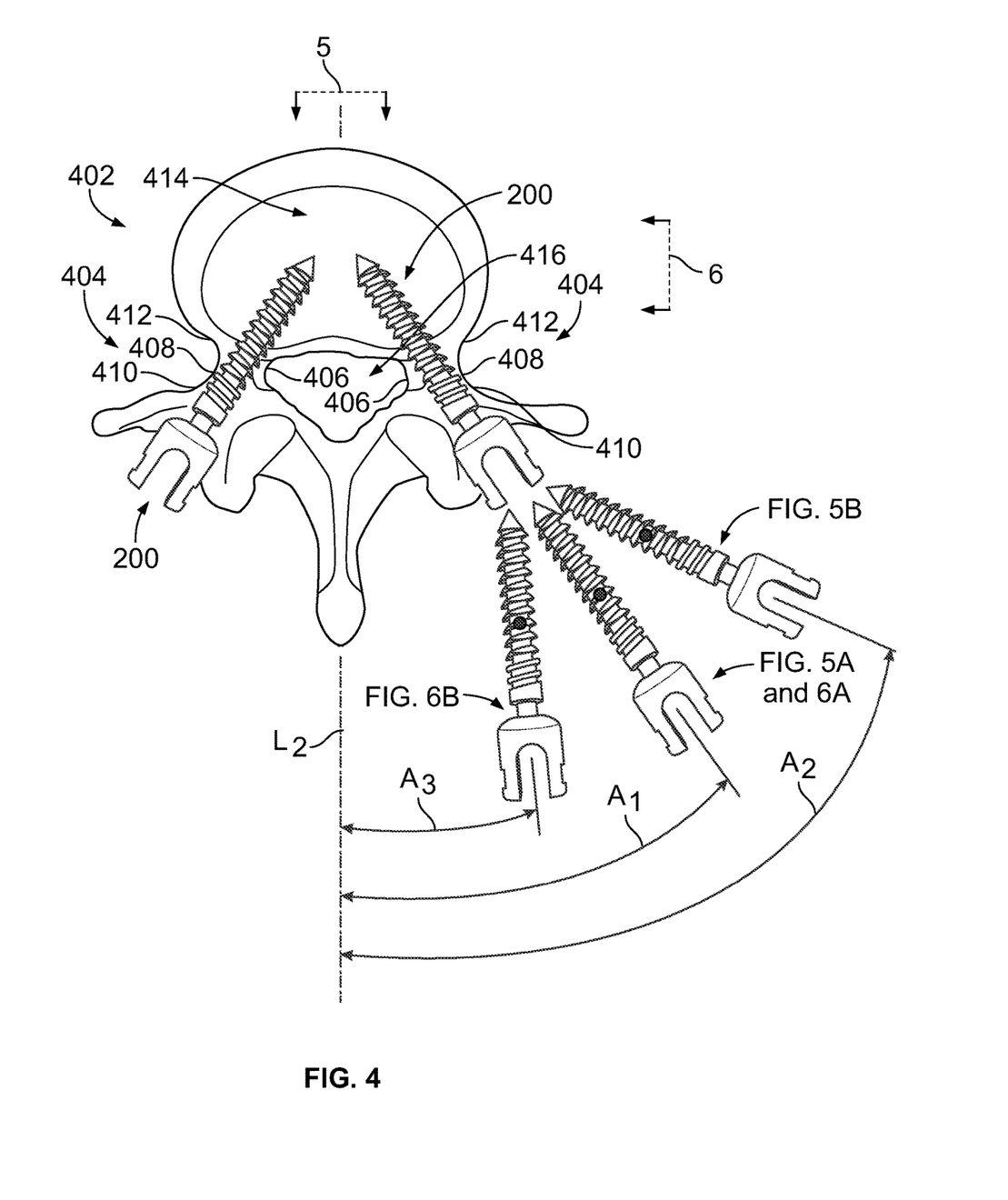
FIG. 4 is a superior view of a vertebra with pedicle screws inserted therein.

FIG. 4 is a superior view of a vertebra 402 with pedicles 404, each of which contains a pedicle screw 200 that has been properly inserted at an optimal angle. FIG. 4 also illustrates examples of pedicle screws prior to insertion into the vertebra, as discussed in more detail below with respect to FIGS. 5A-6B. The pedicle screws 200 in FIG. 4 may comprise any of the pedicle screws 200A-200E shown in FIGS. 2A-2E and described herein. The vertebra 402 comprises a vertebral body 414 and a spinal canal 416 through which the spinal cord (not shown) passes. A longitudinal axis $L_2$ of the vertebra 402 extends through the vertebral body 414 and the spinal canal 416 and bisects the vertebra 402 into substantially equal halves. The pedicles 404 each comprise a first anatomical landmark and a second anatomical landmark. The first anatomical landmark may comprise a medial edge 406 of the pedicle 404, and the second anatomical landmark may comprise a lateral edge 408 of the pedicle 404. Additionally, the pedicles 404 each comprise a third anatomical landmark and a fourth anatomical landmark. The third anatomical landmark may comprise a posterior edge 410 of the pedicle 404, and the fourth anatomical landmark may comprise an anterior edge 412 of the pedicle 404. As discussed below with respect to FIGS. 5A-6B, these anatomical landmarks may be used to determine an optimal insertion angle for the pedicle screws 200.

FIGS. 5A, 5B, 6A, and 6B depict images 500A, 500B, 600A, 600B representing radiographs of a vertebra 502, 602 with respect to a pedicle screw 200 prior to insertion of the pedicle screw. The pedicle screw 200 may comprise any of the pedicle screws 200A-200E shown in FIGS. 2A-2E and described herein.

Figure 5A:
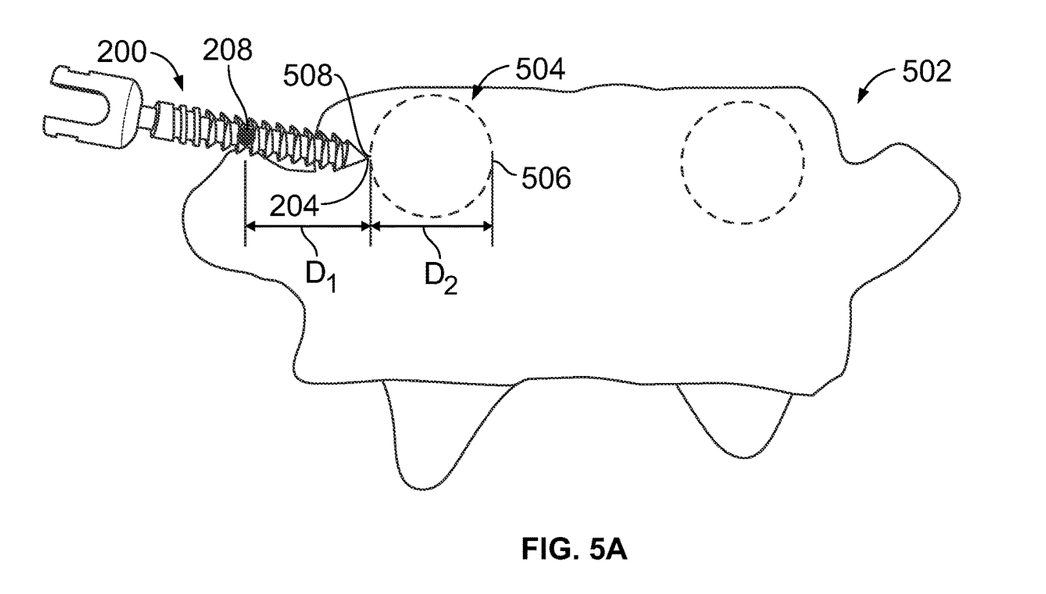
FIGS. 5A, 5B, 6A, and 6B are images representing radiographs of a vertebra with respect to a pedicle screw, in accordance with the present disclosure.
Figure 5B:
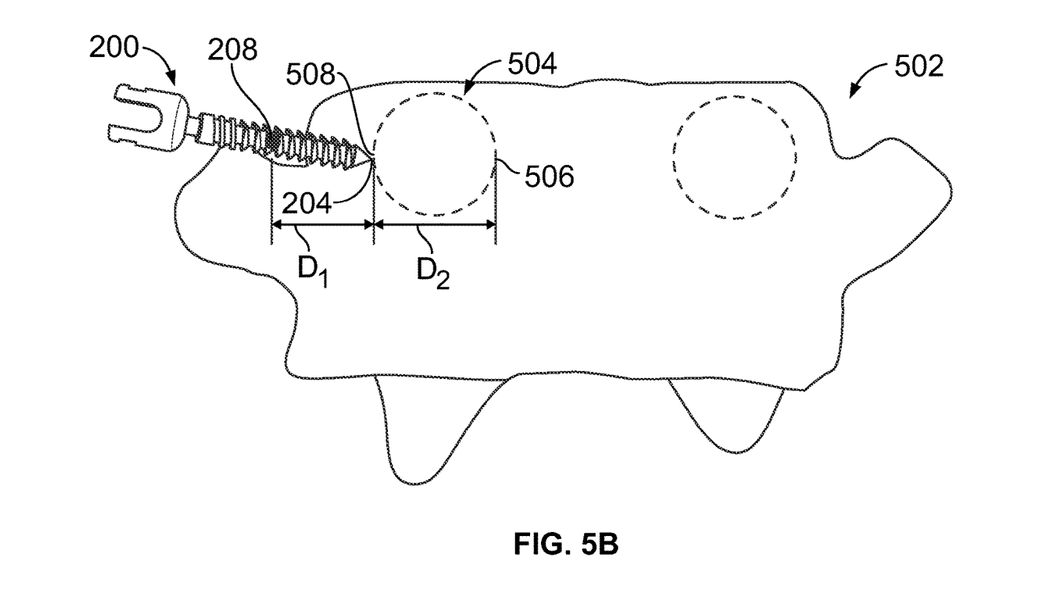

FIGS. 5A and 5B show images 500A, 500B of the vertebra 502 in the AP view, which is taken along view line 5 in FIG. 4. In both images 500A, 500B, the medial edge 506 and the lateral edge 508 of the pedicle 504 are shown in solid lines and the remainder of the vertebra 502 is shown in dashed lines. In some examples, the AP view may comprise the first view. The vertebra 502 may comprise a pedicle 504, which may have a medial edge 506 and a lateral edge 508. Although only one pedicle 504 is labeled, the vertebra 502 includes two pedicles, either of which may receive the pedicle screw 200. As discussed above, the optimal angle for insertion of the pedicle screw 200 is found by comparing the first distance D1 and a second distance D2. The first distance D1 is measured between the radiographically visible element 208 and the distal tip 204. The second distance D2 is measured between the medial edge 506 and the lateral edge 508 of the pedicle 504. When the pedicle screw 200 is positioned as shown in FIGS. 4 and 5A, the first distance D1 and the second distance D2 are equal, such that a current insertion angle A1 is optimal for insertion. Conversely, when the pedicle screw 200 is positioned as shown in FIGS. 4 and 5B, the pedicle screw 200 is positioned laterally with respect to the optimal insertion angle A1. Thus, the first distance D1 is different from, i.e., smaller than, the second distance D2, and a current insertion angle A2 is incorrect.

Figure 6A:
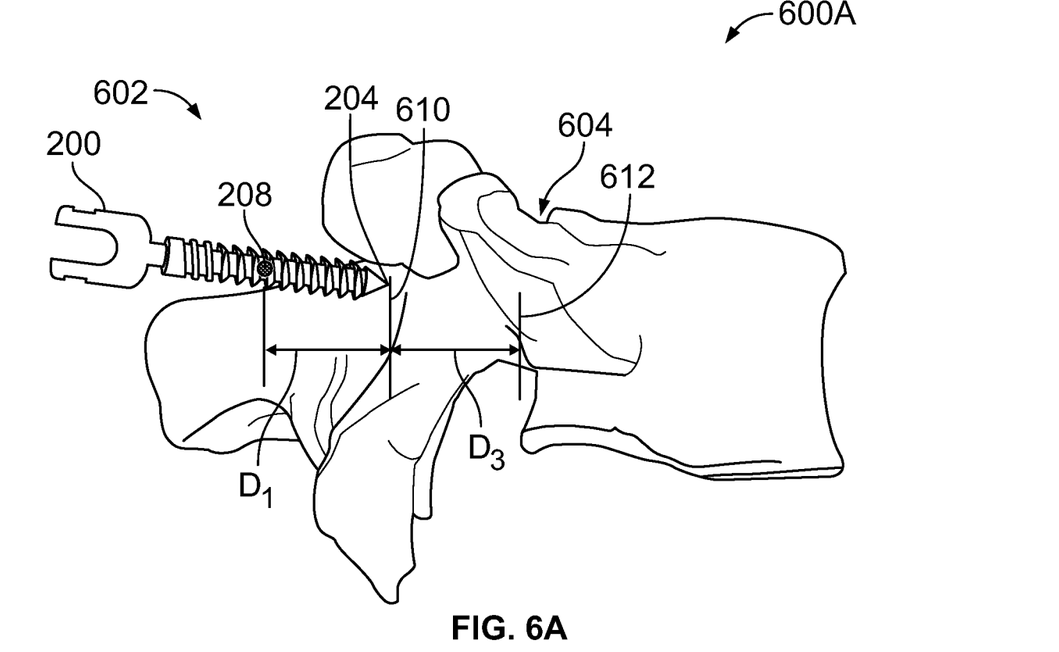
Figure 6B:
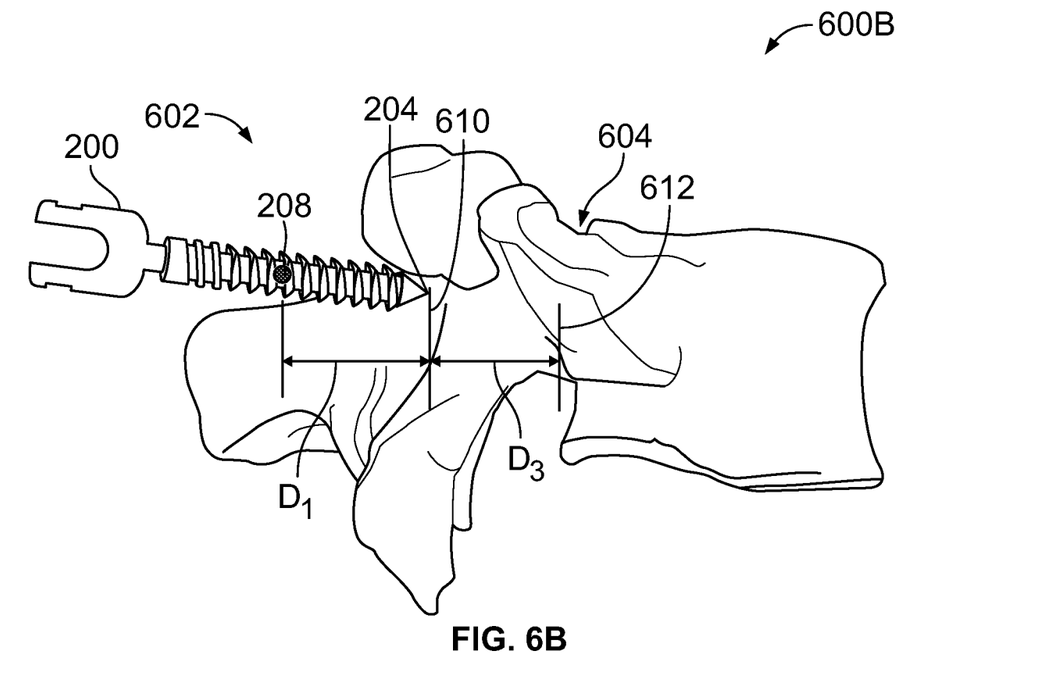

FIGS. 6A and 6B show images 600A, 600B of the vertebra 602 in the lateral view, which is taken along view line 6 in FIG. 4. In some examples, the lateral view may comprise the second view. The vertebra 602 may comprise a pedicle 604, which may have a posterior edge 610 and an anterior edge 612. As discussed above, the optimal angle for insertion of the pedicle screw 200 is found by comparing the first distance D1 and a third distance D3. The first distance D1 is measured between the radiographically visible element 208 and the distal tip 204. The third distance D3 is measured between the posterior edge 610 and the anterior edge 612 of the pedicle 604. When the pedicle screw 200 is positioned as shown in FIGS. 4 and 6A, the first distance D1 and the third distance D3 are equal, such that the current insertion angle A1 is optimal for insertion. Conversely, when the pedicle screw 200 is positioned as shown in FIGS. 4 and 6B, the pedicle screw 200 is positioned medially with respect to the optimal insertion angle A1, such that the first distance D1 is different from, i.e., larger than, the third distance D3 and a current insertion angle A3 is incorrect. While the AP view of FIG. 5B is used to illustrate lateral displacement of the pedicle screw 200 and the lateral view of FIG. 6B is used to illustrate medial displacement of the pedicle screw 200, it may be understood that the AP view may be used to visualize medial displacement and/or the lateral view may be used to visualize lateral displacement. Without intending to be bound by theory, it is believed that optimal placement of the pedicle screw 200 occurs when the distal tip 204 travels the second distance D2 and the third distance D3 concurrently.

The pedicle screw, system, and methods in accordance with the present disclosure may help to optimize the insertion of the pedicle screw. In the example system and methods described above, the pedicle screw with the radiographically visible element may be inserted using the insertion tool and the radiographic imaging device. Conventional systems and methods utilize guide pins or guide wires, computers, and robots, which may increase the complexity, duration, and cost of the procedure.

The description of the present disclosure has been presented for purposes of illustration and description, but is not intended to be exhaustive or limited only to the embodiments in the form disclosed. Many modifications and variations will be apparent to those of ordinary skill in the art without departing from the scope and spirit of the invention.

Having thus described the invention of the present application in detail and by reference to embodiments thereof, it will be apparent that modifications and variations are possible without departing from the scope of the invention defined in the appended claims.

What is claimed is:

1. A method for inserting a pedicle screw into a vertebra, the method comprising:
   introducing a pedicle screw into a soft tissue of a patient, wherein the pedicle screw comprises:
   a head;
   a distal tip;
   a threaded portion extending at least partially between the head and the distal tip; and
   a radiographically visible element located at a predefined location on the threaded portion;
   capturing a first radiographic image of the pedicle screw with respect to the vertebra;
   determining a first distance in the first radiographic image, wherein the first distance is between the distal tip and the radiographically visible element;
   determining a second distance in the first radiographic image, wherein the second distance is between a first anatomical landmark of a pedicle of the vertebra and a second anatomical landmark of a pedicle of the vertebra;
   comparing the first distance and the second distance; and
   when the first distance is equal to the second distance, determining that a current insertion angle is optimal, and at least partially inserting the pedicle screw into the vertebra along the current insertion angle.

2. The method of claim 1, wherein introducing the pedicle screw into the soft tissue of the patient comprises introducing the pedicle screw until the distal tip touches but does not enter the vertebra.

3. The method of claim 1, further comprising:
   partially inserting the pedicle screw into the vertebra; and
   after partially inserting the pedicle screw, capturing at least one additional radiographic image of the pedicle screw with respect to the vertebra.

4. The method of claim 1, wherein when the first and second distances are different, the method further comprises:
   adjusting the current insertion angle of the pedicle screw to a second insertion angle.

5. The method of claim 4, further comprising:
   after adjusting the pedicle screw to the second insertion angle, capturing a second radiographic image of the pedicle screw with respect to the vertebra;
   re-determining the first and second distances in the second radiographic image;
   comparing the first and second distances obtained from the second radiographic image; and
   when the first and second distances obtained from the second radiographic image are equal:
     determining that the second insertion angle is optimal; and
     inserting the pedicle screw into the vertebra along the second insertion angle.

6. The method of claim 1, wherein the first radiographic image comprises a first view of the vertebra, the method further comprising:
   capturing at least one additional radiographic image of the pedicle screw with respect to the vertebra, wherein the at least one additional radiographic image comprises a second view of the vertebra that is different from the first view.

7. The method of claim 6, wherein the first and second views comprise an anteroposterior (AP) view and a lateral view.

8. The method of claim 7, wherein the first view comprises the AP view and the second distance is between a lateral edge of the pedicle of the vertebra and a medial edge of the pedicle of the vertebra in the AP view.

9. The method of claim 7, wherein the second view comprises the lateral view, the method further comprising:
   determining a third distance in the lateral view, wherein the third distance is between a third anatomical landmark of the pedicle of the vertebra and a fourth anatomical landmark of the pedicle of the vertebra; and
   comparing the first distance and the third distance;

wherein determining that the current insertion angle is optimal further comprises determining that the first distance is equal to the third distance.

10. The method of claim 9, wherein the third distance is between an anterior edge of the pedicle of the vertebra and a posterior edge of the pedicle of the vertebra.

\* \* \* \* \*